(12) United States Patent
Hermansson et al.

(10) Patent No.: US 6,685,686 B2
(45) Date of Patent: Feb. 3, 2004

(54) ABSORBENT ARTICLE

(75) Inventors: Kent Hermansson, Vastra Frolunda (SE); Sofia Roxendal, Pixbo (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/074,006

(22) Filed: Feb. 14, 2002

(65) Prior Publication Data

US 2002/0115974 A1 Aug. 22, 2002

Related U.S. Application Data

(60) Provisional application No. 60/268,919, filed on Feb. 16, 2001.

(30) Foreign Application Priority Data

Feb. 16, 2001 (SE) ................................................ 0100532

(51) Int. Cl.$^7$ ................................................ A61F 13/15
(52) U.S. Cl. ................................ 604/385.101; 604/372; 604/382; 604/381
(58) Field of Search .................... 604/385.01, 365, 604/372, 383, 385.101, 381, 382; 428/317.1, 317.3, 315.9, 317.7, 317.5; 156/308.4, 325

(56) References Cited

U.S. PATENT DOCUMENTS

| 4,073,852 | A |   | 2/1978 | Mesek |             |
|-----------|---|---|--------|-------|-------------|
| 4,200,103 | A | * | 4/1980 | Black et al. | 604/366 |
| H1670     | H | * | 7/1997 | Aziz et al.  | 604/367 |
| 5,885,266 | A |   | 3/1999 | Chihani et al. |         |
| 6,015,935 | A | * | 1/2000 | LaVon et al. | 604/378 |
| 6,291,050 | B1 | * | 9/2001 | Cree et al.  | 428/131 |
| 6,380,292 | B1 | * | 4/2002 | Gibes et al. | 524/318 |
| 6,440,112 | B1 | * | 8/2002 | Glaug et al. | 604/385.01 |
| 6,475,199 | B1 | * | 11/2002 | Gann et al. | 604/385.01 |

FOREIGN PATENT DOCUMENTS

| EP | 0 970 710 A1 | 1/2000 |
| EP | 1 022 007 A2 | 1/2000 |
| EP | 0 822 794 B1 | 7/2000 |
| EP | 1 065 047 A1 | 1/2001 |
| SE | 503 798 | 4/1996 |
| WO | 96/33679 | 10/1996 |
| WO | 98/42290 | 10/1998 |
| WO | WO 2/34188 | 5/2002 |

* cited by examiner

Primary Examiner—Weilun Lo
Assistant Examiner—Jacqueline Stephens
(74) Attorney, Agent, or Firm—Young & Thompson

(57) ABSTRACT

Absorbent article such as a diaper, an incontinence guard, a pantyliner or a sanitary napkin, including a liquid-pervious topsheet (3), a liquid-impermeable backsheet (2), and an absorbent body (4) enclosed therebetween, wherein the topsheet (3) and absorbent body (4) either directly or via at least one intermediate layer are joined partly by a first adhesive (5) and partly by a second adhesive (6) The surface which is constituted of the topsheet (3) and which is adhesively joined with the first adhesive (5) and the second adhesive (6) is formed into a three-dimensional structure having alternating raised (8) and recessed regions (7), wherein the first adhesive (5) is arranged in the recessed regions (7) and the second adhesive (6) is arranged in the raised regions (8).

19 Claims, 2 Drawing Sheets

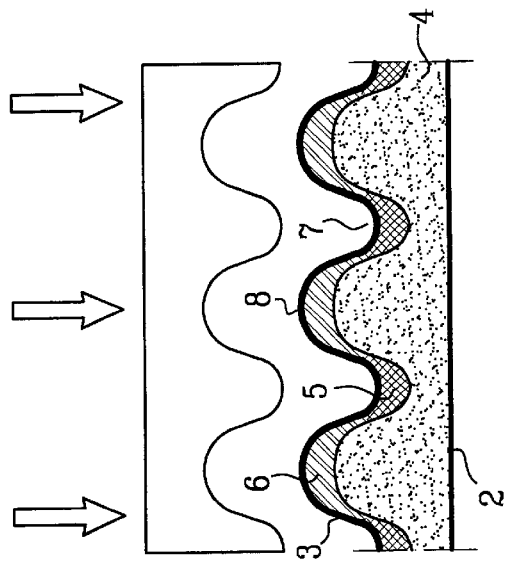
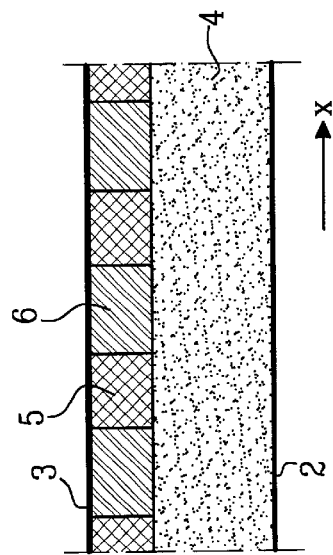
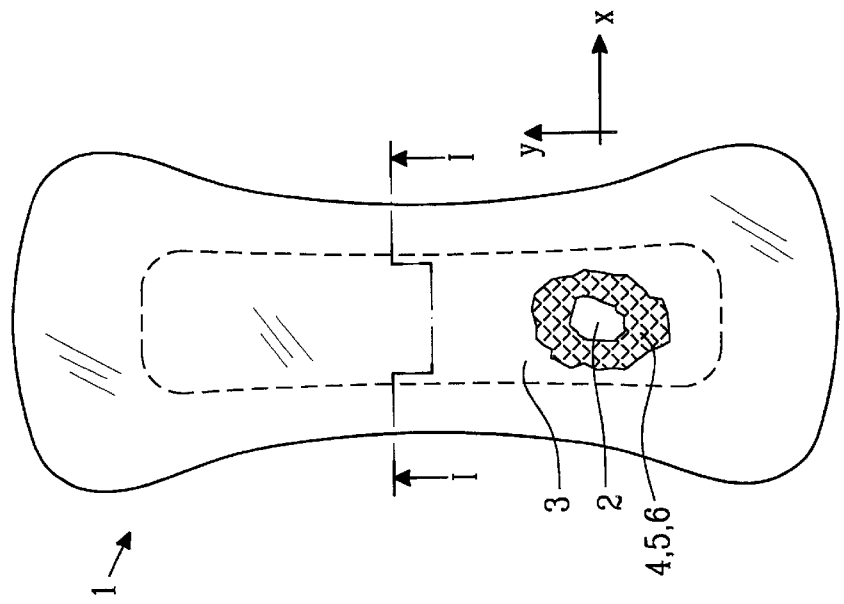

ABSORBENT ARTICLE

TECHNICAL FIELD

The present invention relates to an absorbent article such as a diaper, an incontinence guard, a pantyliner, or a sanitary napkin comprising a liquid-pervious topsheet, a liquid-impermeable backsheet and an absorbent body enclosed therebetween, wherein said topsheet and absorbent body either directly or via at least one intermediate layer are joined by means of a first adhesive.

BACKGROUND OF THE INVENTION

An absorbent article, such as a diaper, an incontinence guard or a sanitary napkin, normally comprises a liquid-pervious topsheet, a liquid-impermeable backsheet, and an absorbent body enclosed therebetween. Typically, the topsheet is glued to the backsheet by means of a hydrophobic adhesive.

In order to achieve a surface facing towards the user, which has an improved liquid-absorption, different treatments have been proposed for enabling the topsheet to let liquid pass through more rapidly to the underlying absorbent body. Nonwoven materials, which often are utilised as topsheets are, as a rule, substantially hydrophobic. These materials can be treated, for example, with surfactants in order to render the material more hydrophilic. However, after wetting of the material, the surfactant is washed away and the topsheet becomes hydrophobic once again. Thereby, the liquid transport through the material is deteriorated.

EP 0 822 794 discloses a method for achieving a three-dimensional structure having ridges and valleys on an article which consists of a liquid-impermeable backsheet, an absorbent core, and a liquid-impermeable topsheet. The topsheet with the underlying absorbent body are provided with a pattern by means of embossed rolls and which create a pattern comprising said ridges and valleys. This topology is intended to guide the liquid down into the absorbent core. In a second rolling treatment, a penetrating agent is applied in order to neutralize the hydrophobic fibres in the topsheet and create contact, in the form of hydrophilic flow lines, with the hydrophilic fibres in the absorbent body.

However, a prerequisite for a good transport of liquid from the topsheet to the absorbent body is that said layer really is in contact with the absorbent body, either directly or via an underlying liquid transfer layer. An air gap may be created between the topsheet and the absorbent body or, alternatively, there may be air between the three different layers constituted of the topsheet, the underlying liquid transfer layer and the absorbent body, something that considerably impairs the liquid aqcuisition into the absorbent body. In order to ensure that the absorbent body really contacts and remains in contact with the topsheet, the topsheet and the absorbent body can be joined by means of an adhesive. For this purpose, either a hydrophobic or a hydrophilic adhesive can be utilised.

SE 503 798 discloses an absorbent article where the topsheet is glued to the absorbent body by means of a hydrophilic adhesive in order to achieve a surface, which more easily lets liquid through. However, the surface may be perceived as somewhat moist by the wearer during usage.

WO 98/42290 discloses an article, which exhibits a three-dimensional structure having slightly raised flat regions, and recessed regions. Across the raised regions, a hydrophobic material has been applied on top of the topsheet, which causes the liquid to pass down into the recessed regions. This product, however, has the disadvantage that the hydrophobic material has to be applied on the topsheet, something that requires an additional step in the production of absorbent articles when the choice of material and equipment is concerned.

Accordingly, there is a need for a product which provides a rapid liquid acquisition and which the user perceives as having a dry surface.

SUMMARY OF THE INVENTION

The object of the present invention is to provide a product which has good liquid absorption ability, and which still exhibits a dry surface facing towards the user. This object is achieved by means of using a second adhesive, which is more hydrophobic than said first adhesive, for joining said topsheet and absorbent body, either directly or via at least one intermediate layer. The liquid which is to be absorbed is guided from the more hydrophobic regions created in this way, which repel an aqueous solution, to the comparatively more hydrophilic regions, where the liquid is directed further down to and is absorbed into the absorbent body.

Preferably, the first and the second adhesive are arranged in patterns, wherein the pattern of the first adhesive, at least to a substantial extent, does not coincide with the pattern of the second adhesive, but is displaced in relation to this.

According to another aspect of the invention, the adhesively joined portion of the topsheet, alternatively together with at least one intermediate layer, which overlaps the absorbent body, can be formed into a three-dimensional structure. This results in a product, which preferably has raised hydrophobic regions and recessed hydrophilic regions. The liquid that is to be absorbed is guided down onto the hydrophilic recessed regions where the liquid will be absorbed into the underlying absorbent body, whereas the hydrophobic raised regions will contain less liquid. Consequently, those raised regions that are in closest contact with the skin of the user will be perceived as more dry.

BRIEF DESCRIPTION OF THE DRAWINGS

In the following, the invention will be described in greater detail with reference to embodiments shown in the attached drawings.

FIG. 1 shows a schematic perspective view, seen from above, of an absorbent article according to the present invention.

FIG. 2 shows a cross-section along the line I—I in FIG. 1.

FIG. 3 shows the cross-section in FIG. 2, which has obtained a three-dimensional structure after embossing.

DETAILED DESCRIPTION OF THE INVENTION

Figure 4:
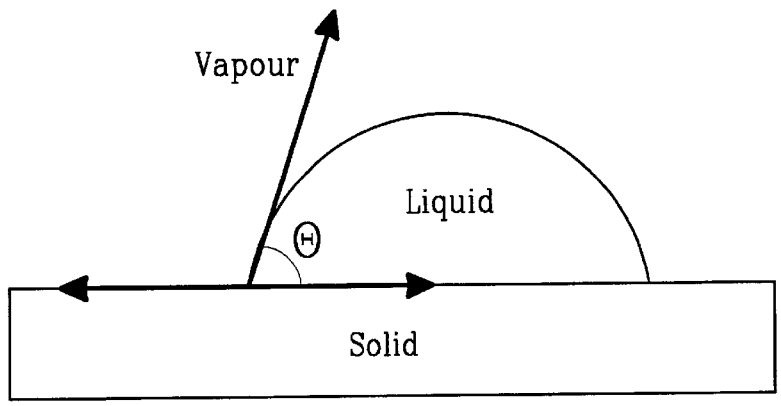
FIG. 4 shows a schematic illustration of a contact angle θ measurement.
Figure 5:
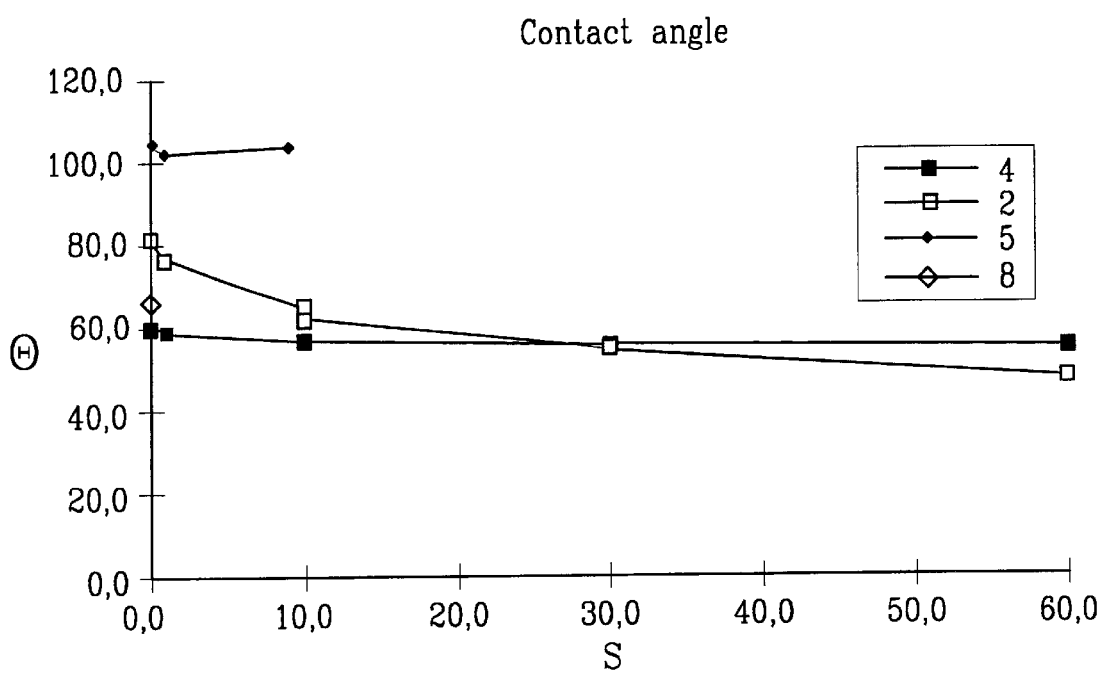
FIG. 5 shows results from experiments for determining the contact angle of adhesives according to Example 1.

The drawing shows an embodiment of an absorbent article, which can be a diaper, an incontinence guard, a pantyliner or a sanitary napkin 1, comprising a liquid-impermeable backsheet 2, a liquid-pervious topsheet 3, and an absorbent body 4 enclosed therebetween. The liquid-pervious topsheet 3 can consist of a nonwoven material, e.g. a spunbond-material of continuous filaments, a meltblownmaterial, a bonded, carded fibre material, or a tow-material. The liquid-impermeable backsheet 2 can consist of a plastic film, a nonwoven material, which has been coated with a liquid-barrier material, or a hydrophobic nonwoven material, which resists liquid penetration.

The backsheet 2 and the topsheet 3 have a somewhat larger extension in the plane than the absorbent body 4, and extend beyond its edges. The layers 2 and 3 are mutually inter-connected within the protruding portions, for example by means of gluing or welding by means of heat or ultrasonics.

The absorbent body 4 can be of any conventional type. Examples of commonly occurring absorption materials are cellulose fluff pulp, tissue layers, highly absorbent polymers (so-called superabsorbents), absorbent foam materials, absorbent nonwoven materials and the like. It is common to combine cellulose fluff pulp with superabsorbents in an absorbent body. It is also common with absorbent bodies constituted of layers of different materials having different properties when liquid acquisition ability, distributing ability and storage capacity are concerned. This is well known to the skilled person within the field, and is therefore not necessary to describe in detail. The thin absorbent cores, which are common for example in baby diapers, incontinence guards and sanitary napkins, usually consist of a compressed mixed or layered structure of cellulose fluff pulp and superabsorbent.

The topsheet 3 does not have to be directly bonded to the absorbent body 4. It is e.g. possible to create a laminate of a topsheet and an underlying liquid transfer layer such as a wadding, a bulky nonwoven, or the like. Thereafter, such a laminate can be attached to the absorbent body in a conventional way, e.g. by means of gluing. Liquid transfer layers constitute a component of absorbent articles which both can be counted to the topsheet and to the absorbent body. Commonly utilised materials in liquid transfer layers are polyester waddings, porous nonwoven materials, tow-materials, air-laid bonded cellulose layers, etc. Accordingly, when describing the different embodiments, the present invention is intended to include also a possible occurrence of at least one such underlying liquid transfer layer between the topsheet 3 and the absorbent body 4.

In the article according to the invention, the contacting surfaces of the liquid-pervious topsheet 3 and the absorbent body 4 are joined by means of a first adhesive 5 and a second adhesive 6. Preferably, said first adhesive 5 consists of a substantially hydrophilic adhesive. Said second adhesive 6 can consist of a substantially hydrophobic adhesive. The main thing, however, is that said second adhesive 6 has a more hydrophobic nature than said first adhesive 5.

The hydrophobic or hydrophilic nature of the adhesives can be determined by means of a so-called contact angle test. An adhesive can be regarded as hydrophobic if it exhibits a contact angle $\theta$, which exceeds 90°. See Example 1 for details concerning the test. The first adhesive 5 should exhibit a contact angle $\theta$, which is smaller than the contact angle $\theta$ of the second adhesive 6. It is preferred that the first adhesive 5 exhibits a contact angle $\theta$ which is at least 10° smaller than the second adhesive 6. Preferably, the first adhesive 5 exhibits a contact angle $\theta$, which is at least 20° smaller than the second adhesive 6. It is even more preferred that the first adhesive 5 exhibits a contact angle $\theta$ which is at least 30° smaller than the second adhesive 6. In another embodiment, the first adhesive 5 exhibits a contact angle $\theta$ which is smaller than 90°, and the second adhesive 6 exhibits a contact angle which exceeds 90°.

FIG. 2 shows a cross-section through the article. This shows how the first adhesive 5 and the second adhesive 6, which is arranged between the topsheet 3 and the absorbent body 4, are arranged in a pattern, wherein the pattern of the first adhesive 5, at least to a substantial extent, does not coincide with the pattern of the second adhesive 6 but is displaced in relation to this. The pattern can be constituted of e.g. stripes or squares, where the different adhesives assume alternating positions, seen along the x- and/or y-direction. Thereby, the term x-direction means transversely to the longitudinal direction of the article, which is defined as a front portion, a rear portion and a crotch portion located therebetween. The term y-direction means along the longitudinal direction of the article.

FIG. 3 shows, in cross-section, how the article has obtained a three-dimensional structure after embossing. This structure exhibits recessed regions 7 and raised regions 8. Said first adhesive 5 is arranged in the recessed regions 7 and said second adhesive 6 is arranged in the raised regions 8.

The embossing can be accomplished by means of grooves, which are placed in the positions where the first adhesive is located. These areas will then constitute the recessed regions 7 in the three-dimensional structure. Furthermore, the structure can be a waffle structure where the two adhesives substantially are arranged in a checkered pattern. Furthermore, the positions of the recessed regions 7 and the raised regions 8 in one row can be displaced in the x-direction in relation to the next row. The adhesives could also be applied in a substantially wave-like structure along the longitudinal direction of the article.

In case the topsheet 3 is constituted of a material which in itself has a three-dimensional structure with alternating raised and recessed portions, for example which is bonded in a certain binding pattern where the binding points constitute the recessed portions 7, the more hydrophilic adhesive can be applied at the binding points and the more hydrophobic one at the raised portions 8 between the binding points.

Said three-dimensional structure could also be achieved by means of adhesives, which for example during curing or heat treatment shrink differently, something that will create a three-dimensional structure having raised and recessed regions.

According to another embodiment, the article can have a liquid acquisition zone with a more dense distribution of recessed hydrophilic areas that, for example, can be located in the central portion of the article. This can be achieved by means of the adhesives being arranged in an irregular pattern, or by means of the embossing taking place only on part of the adhesively joined portion of the article.

When the article is used and a liquid ends up on the embossed topsheet 3 which has been adhesively joined to the absorbent body 4, the liquid will be able to flow along the hydrophobic raised portion 8 down onto the more hydrophilic, recessed portion 7. From there, the liquid rapidly will be able to rapidly penetrate down through the topsheet 3 and further to be absorbed into the absorbent core 4. A minor absorption will of course also take place in the raised regions 8, but the main part of the liquid will find its way to the recessed areas 7 for further absorption into the product. As a result, the raised areas 8 which are in closest contact against the skin will contain less liquid and thereby be perceived drier by the user. Furthermore, the three-dimensional structure allows a minor airflow between the wearer and the article through the recessed regions 7, something which results in the product being perceived as more dry.

The three-dimensionally shaped topsheet 3 with its recessed and raised areas also provides a more favourable rewetting environment, since the raised regions are adhesively joined using a hydrophobic adhesive, which counteracts liquid transport out from the article. Furthermore, the embossing creates a distance between the body of the user and the liquid absorbed into the article.

In the following, the invention will be illustrated in greater detail by means of the following example.

EXAMPLE 1

Contact Angle Measurement on Adhesives

In order to be regarded as hydrophilic, a material such as e.g. an adhesive shall have a contact angle θ between a liquid and the material, which is to be measured which is smaller than 90°. The contact angle between a test liquid in contact with a substrate such as a nonwoven material can be measured by means of a DAT (dynamic absorption tester).

Four different adhesives were applied onto a paper having a grammage of 80 g/m². Thereafter, the specimens were cut into 25 mm wide strips. A small droplet is applied onto the surface of the test substrate by means of a microsyringe. A camera captures images of the droplet during a number of time intervals. The contact angle θ is measured as a function of time. Two different tests were performed: one measurement at 0.1, 1.0 and 10 seconds, and one measurement at 10.0, 30.0 and 60.0 seconds.

The following adhesives were tested:
2. Hydrophilic dispersion adhesive based on polyvinyl acetate, stabilised with polyvinyl alcohol.
4. Hydrophilic dispersion adhesive based on a partially cross-linked ethylene vinylacetate co-polymer.
5. Hydrophobic melt-adhesive based on an atactic poly-α-olefin.
8. Hydrophobic melt-adhesive based on an atactic polypropylene and a nonionic surfactant.

The results (see FIG. 4) proved that adhesive No. 5 has a contact angle θ which exceeds 90°, i.e. this material is hydrophobic, and also that the other adhesives 2, 4 and 8 have a contact angle θ which is smaller than 90°, i.e., they are hydrophilic adhesives.

The invention is of course not limited to the embodiments described above and shown in the drawings, but can be varied within the scope of the following claims.

What is claimed is:

1. An absorbent article selected from the group consisting of a diaper, an incontinence guard, a pantyliner, and a sanitary napkin, the article comprising a liquid-pervious topsheet, a liquid-impermeable backsheet, and an absorbent body enclosed therebetween; a first adhesive joining said topsheet and absorbent body either directly or via at least one intermediate layer; a second adhesive joining said topsheet and absorbent body, either directly or via said intermediate layer; said second adhesive being more hydrophobic than said first adhesive; whereby a surface, which is constituted of said topsheet and which is adhesively joined using said first adhesive and said second adhesive, is formed into a three-dimensional structure exhibiting alternating raised and recessed regions; said first adhesive being arranged in the recessed regions, and said second adhesive being arranged in the raised regions.

2. The article according to claim 1, wherein said first adhesive consists of a substantially hydrophilic adhesive.

3. The article according to claim 1, wherein said second adhesive consists of a substantially hydrophobic adhesive.

4. The article according to claim 1, wherein said first adhesive and said second adhesive are arranged in patterns, wherein the pattern of the first adhesive, at least to a substantial extent, does not coincide with the pattern of the second adhesive, but is displaced in relation thereto.

5. The article according to claim 1, wherein the first adhesive exhibits a contact angle θ which is smaller than the contact angle θ of the second adhesive.

6. The article according to claim 1, wherein the first adhesive exhibits a contact angle θ which is at least 10° smaller than the contact angle θ of the second adhesive.

7. The article according to claim 1, wherein the first adhesive exhibits a contact angle θ which is at least 20° smaller than the contact angle θ of the second adhesive.

8. The article according to claim 1, wherein the first adhesive exhibits a contact angle θ which is at least 30° smaller than the contact angle θ of the second adhesive.

9. The article according to claim 1, wherein the first adhesive exhibits a contact angle θ which is smaller than 90°, and the second adhesive exhibits a contact angle θ which is greater than 90°.

10. An absorbent article selected form the group consisting of a diaper, an incontinence guard, a pantyliner, and a sanitary napkin, the article comprising a liquid-pervious topsheet, a liquid-impermeable backsheet, and an absorbent body enclosed therebetween; a first adhesive joining said topsheet and absorbent body either directly or via at least one intermediate layer; a second adhesive joining said topsheet and absorbent body, either directly or via said intermediate layer; said second adhesive being more hydrophobic than said first adhesive; wherein an upper surface of said topsheet is continuous and forms a three-dimensional structure exhibiting alternating raised and recessed regions.

11. The article according to claim 10, wherein said first adhesive consists of a substantially hydrophilic adhesive.

12. The article according to claim 10, wherein said second adhesive consists of a substantially hydrophobic adhesive.

13. The article according to claim 10, wherein said first adhesive and said second adhesive are arranged in patterns, wherein the pattern of the first adhesive, at least to a substantial extent, does not coincide with the pattern of the second adhesive, but is displaced in relation thereto.

14. The article according to claim 10, wherein said surface exhibits recessed regions and raised regions, said first adhesive being arranged in the recessed regions, and said second adhesive being arranged in the raised regions.

15. The article according to claim 10, wherein the first adhesive exhibits a contact angle θ which is smaller than the contact angle θ of the second adhesive.

16. The article according to claim 10, wherein the first adhesive exhibits a contact angle θ which is at least 10° smaller than the contact angle θ of the second adhesive.

17. The article according to claim 10, wherein the first adhesive exhibits a contact angle θ which is at least 20° smaller than the contact angle θ of the second adhesive.

18. The article according to claim 10, wherein the first adhesive exhibits a contact angle θ which is at least 30° smaller than the contact angle θ of the second adhesive.

19. The article according to claim 10, wherein the first adhesive exhibits a contact angle θ which is smaller than 90°, and the second adhesive exhibits a contact angle θ which is greater than 90°.

* * * * *